(12) United States Patent
Xie et al.

(10) Patent No.: US 6,774,273 B2
(45) Date of Patent: Aug. 10, 2004

(54) PROCESS FOR SELECTIVE DISPROPORTIONATION OF TOLUENE AND DISPROPORTIONATION AND TRANSALKYLATION OF TOLUENE AND C9+ AROMATICS

(75) Inventors: Zaiku Xie, Shanghai (CN); Weisheng Yang, Shanghai (CN); Dejin Kong, Shanghai (CN); Dongmao Zhu, Shanghai (CN)

(73) Assignee: China Petroleum & Chemical Corporation, Beijing (CN)

( * ) Notice: Subject to any disclaimer, the term of this patent is extended or adjusted under 35 U.S.C. 154(b) by 23 days.

(21) Appl. No.: 10/277,694

(22) Filed: Oct. 22, 2002

(65) Prior Publication Data
US 2003/0130549 A1 Jul. 10, 2003

(30) Foreign Application Priority Data
Oct. 22, 2001 (CN) ........................................ 01131953 A (51) Int. Cl.[7] ................................................ C07C 2/66
(52) U.S. Cl. ...................... 585/304; 585/300; 585/303; 585/470; 585/475
(58) Field of Search ................................. 585/300, 303, 585/304, 470, 475

(56) References Cited

U.S. PATENT DOCUMENTS

| | | | |
|---|---|---|---|
| 2,795,629 A | 6/1957 | Boedeker | 260/668 |
| 3,551,510 A | 12/1970 | Polltzer et al. | 260/672 |
| 3,780,122 A | 12/1973 | Pollitzer | 260/672 |
| 4,341,914 A | 7/1982 | Berger | 585/474 |
| 4,343,914 A | 8/1982 | Lee | 521/168 |
| 4,665,258 A | 5/1987 | Butler et al. | 585/475 |

FOREIGN PATENT DOCUMENTS

| | | | |
|---|---|---|---|
| CN | 1050011 | 3/1991 | B01J/29/18 |
| CN | 1217369 | 5/1999 | C10G/35/04 |
| CN | 1235948 | 11/1999 | C07C/15/04 |
| JP | 49-46295 | 12/1973 | C07E/3/62 |

Primary Examiner—Thuan D Dang
(74) Attorney, Agent, or Firm—Cohen, Pontani, Lieberman & Pavane (57) ABSTRACT

The present invention relates to a process for the selective disproportionation of toluene and the disproportionation and transalkylation of toluene and $C_9^+$ aromatics to mainly solve the problems in the prior arts of the great amount of recycle stream, high energy consumption or harsh requirement for the reaction feedstocks. The present invention has better solved these problems by the technical solution using a process for selective disproportionation of toluene to produce mixed xylenes containing a high concentration of p-xylene, and subsequent disproportionation and transalkylation of $C_9^+$ aromatics and toluene to produce benzene and the mixed xylenes which are in the thermodynamic equilibrium. The process is applicable to the industrial production.

20 Claims, 2 Drawing Sheets

FIG. 1

PRIOR ART

FIG. 2

PROCESS FOR SELECTIVE DISPROPORTIONATION OF TOLUENE AND DISPROPORTIONATION AND TRANSALKYLATION OF TOLUENE AND C9+ AROMATICS

PRIORITY CLAIM

This application claims priority from China Patent Application Number 01131953.4 which was filed on Oct. 22, 2001.

BACKGROUND OF THE INVENTION

1. Field of the Invention

The present invention relates to a process for the selective disproportionation of toluene, and the disproportionation and transalkylation of toluene and $C_9^+$ aromatics ($C_9^+A$), in particular it relates to a process for the selective disproportionation of toluene, and the disproportionation and transalkylation of toluene and $C_9^+$ aromatics followed by a process for producing p-xylene (PX) by a technique of the isomerization of $C_8$ aromatics ($C_8A$) and a technique of p-xylene separation.

Figure 1:
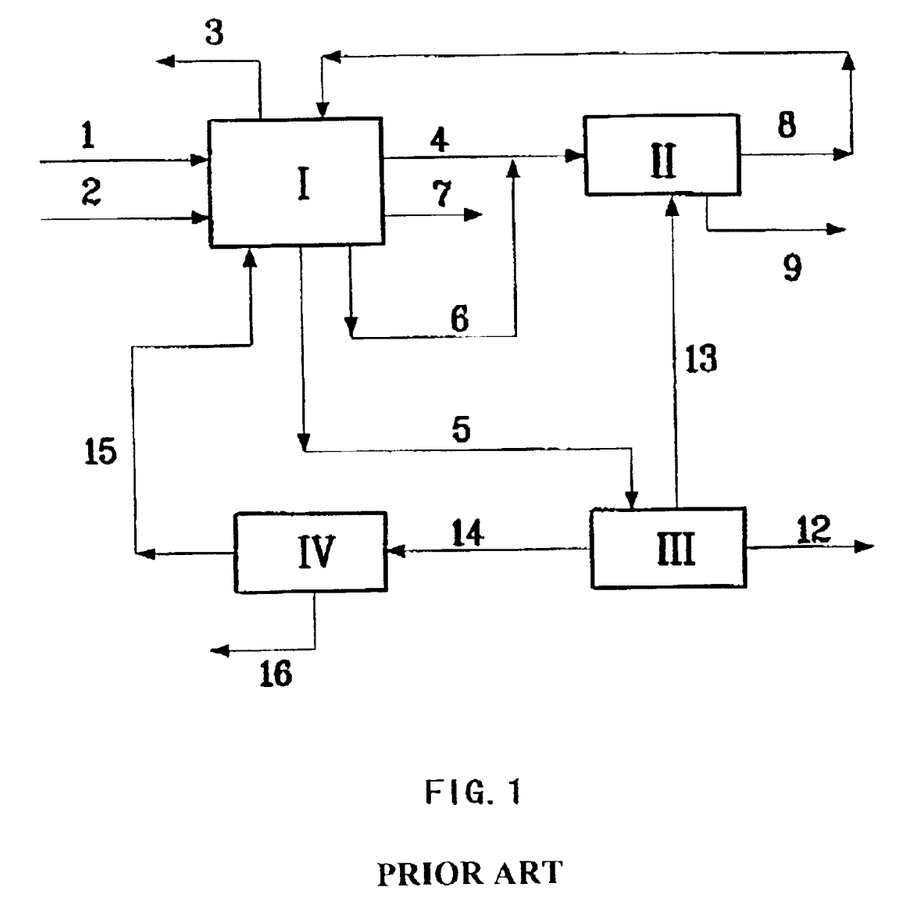
FIG. 1 is the flow diagram of the traditional complex for aromatics production.

2. Description of the Related Art p-xylene is one of the major basic organic feedstocks in petrochemical industry and has widespread applications in many fields such as chemical fiber, synthetic resin, pesticide, medicine, plastic, etc. The traditional process for producing p-xylene is shown in FIG. 1. $C_8$ aromatics ($C_8A$) in thermodynamic equilibrium produced from the catalytic reforming process of naphtha passes through a multi-stage subzero crystallization separation or molecular sieve simulation moving bed separation (abbreviated as adsorptive separation) to separate p-xylene from its isomer mixture with near boiling points. A $C_8A$ isomerization (abbreviated as isomerization) process is generally used to isomerize o-xylene and m-xylene to p-xylene. The use of disproportionation of toluene, or the disproportionation and transalkylation of toluene and $C_9^+$ aromatics ($C_9^+A$) to produce benzene and $C_8A$, is an effective route for increasing the output of p-xylene.

So far, the typical and mature processes relating to toluene disproportionation in the world are the Tatoray traditional toluene disproportionation process of UOP Inc. industrialized in the end of 1960s, the MTDP process of Mobil Chemical Company developed in the end of 1980s, the S-TDT process of Shanghai Institute of Petrochemical Industry developed recently, and the TransPlus transalkylation process of heavy aromatics of Mobil Chemical Company. The selective disproportionation of toluene is a new route for producing p-xylene. Since the selective disproportionation of toluene on modified ZSM-5 catalysts can produce benzene and $C_8A$ with a high concentration of p-xylene, the difficulty in the separation of p-xylene is greatly alleviated. In recent years, along with the improvement of the catalyst performance, this process has made a great progress. The typical processes are the Mobil toluene selective disproportionation process MSTDP industrialized in late 1980s and the UOP toluene selective disproportionation process PX-Plus developed in late 1990s.

In the industrialized toluene selective disproportionation process MSTDP, a converted ZSM-5 mesoporous molecular sieve is used as the catalyst to treat a toluene feedstock yielding $C_8A$ with a high concentration of p-xylene (85–90% by weight, the same below except otherwise noted) and nitration grade benzene. In the PX-Plus process, no industrialization of which has been reported, to applicant's knowledge, the major reaction performance is a PX selectivity of 90%, a mole ratio of benzene to PX of 1.37 in case of the toluene conversion of 30%.

Nevertheless, in these toluene selective disproportionation processes, a high p-xylene selectivity is accompanied by a harsh requirement to the feedstock selection, and only toluene can be used as the feedstock. $C_9^+A$ has no use for these processes, and at least it can not be directly used. This is a vital shortcoming of the selective disproportionation process.

The feed for the reactor of a typical Tatoray process is toluene and $C_9$ aromatics ($C_9^+A$). The xylenes produced in the Tatoray process are a mixture of the isomers in thermodynamic equilibrium, and generally, the content of p-xylene having the most industrial application value is only about 24%. Compared to the selective disproportionation of toluene wherein mixed xylenes having a p-xylene concentration of about 90% can be obtained, the Tatoray process is obviously inferior in this aspect, but a great advantage of the Tatoray process over the toluene selective disproportionation process is that the Tatoray process can convert $C_9A$ to benzene and xylenes.

The literature based on the Tatoray Process includes U.S. Pat. Nos. 4,341,914, 2,795,629, 3,551,510, CN98110859.8, CN97106719.8, etc. The process disclosed by the representative U.S. Pat. No. 4,343,914 comprises conducting the aromatics fractionation of the reformed product, feeding the derived toluene and $C_9A$ to the Tatoray unit to conduct disproportionation and transalkylation reactions, recycling toluene, $C_9A$, and a part of $C_{10}$ aromatics ($C_{10}A$) after separating the products, withdrawing benzene as a product, feeding xylene together with the xylene from the isomerization unit to the PX separation unit to separate the high purity of p-xylene product. The other isomers of xylene are fed to the isomerization unit to conduct the isomerization reaction of xylene, yielding the mixed xylenes in thermodynamic equilibrium again.

One representative aromatics complex based on the selective disproportionation process is the PX-Plus Process. The greatest difference between the PX-Plus Process and the traditional aromatics complex Tatoray process is that $C_9^+A$ is withdrawn as a byproduct instead of as a feed in the PX-Plus process.

It is readily seen from summarizing the above processes that the traditional aromatics production process uses the disproportionation and transalkylation process to attain the object of increasing the output of xylenes, but the amount of the recycled xylenes is large since the produced mixed xylenes are the isomers of xylene in the thermodynamic equilibrium and therefore the concentration of p-xylene is low. The other isomers of xylene have to pass through the isomerization unit to be converted to p-xylene, thus resulting in heavy xylene recycles and high energy consumption in the isomerization unit, PX separation unit and aromatics fractionation unit. Although mixed xylenes with high concentration of p-xylene can be obtained by the aromatics production process using the selective disproportionation process, and thereby the feeds of the isomerization unit and the like are greatly reduced, the selective disproportionation process can not treat $C_9^+A$, which results in a waste of the $C_9^+A$ resource, and a reduced output of the target product, p-xylene.

Therefore, it is very desirable to develop a process for producing high yield of the desire product p-xylene, which does not have harsh strict requirement to the feedstock. It is also desirable to greatly reduce the energy consumption or increase the capacity of processing the feedstock.

SUMMARY OF THE INVENTION

Thus, one object of the present invention is to overcome the shortcomings present in the prior art of low concentration in the mixed xylenes, high energy consumption, or harsh requirement to the reaction feedstock in the production of p-xylene.

Another object of the present invention is to provide a novel process for the selective disproportionation of toluene and the disproportionation and transalkylation of toluene and $C_9^+$ aromatics. The improved economical viability and profitability of producing p-xylene are obtained by increasing the capacity of the whole process and the output of the target products p-xylene and benzene, greatly reducing the scale of the p-xylene separation unit, isomerization unit, and the aromatics fractionation unit, and thereby decreasing the energy consumption of the whole process.

These and other objects are attained by a novel process of the selective disproportionation of toluene and the disproportionation and transalkylation of toluene and $C_9^+$ aromatics comprising:

a) separating a feed stream comprising benzene, toluene, $C_8$ aromatics, and $C_9^+$ aromatics into a first benzene stream, a toluene stream, a first $C_8$ aromatics stream, and a $C_9^+$ aromatics stream;

b) introducing a part of the toluene stream into a toluene selective disproportionation unit to conduct the toluene selective disproportionation reaction for producing a first effluent comprising $C_8$ aromatics rich in p-xylene, and benzene;

c) separating a second $C_8$ aromatics stream and a second benzene stream from the first effluent produced in the step of b);

d) introducing another part of the toluene stream and the $C_9^+$ aromatics stream into a toluene disproportionation and transalkylation unit to conduct the toluene disproportionation and transalkylation reaction in the presence of hydrogen for producing a second effluent comprising $C_8$ aromatics and benzene;

e) separating a third $C_8$ aromatics stream and a third benzene stream from the second effluent produced in the step of d); and f) separating the first, and third $C_8$ aromatics stream into a p-xylene product and a remaining mixed xylenes stream.

Other objects and features of the present invention will become apparent from the following detailed description considered in conjunction with the accompanying drawings. It is to be understood, however, that the drawings are designed solely for purposes of illustration and not as a definition of the limits of the invention, for which reference should be made to the appended claims. It should be further understood that the drawings are not necessarily drawn to scale and that, unless otherwise indicated, they are merely intended to conceptually illustrate procedures described herein.

DETAILED DESCRIPTION OF THE PRESENTLY PREFERRED EMBODIMENTS

Typically, the feed stream comprising benzene, toluene, $C_8$ aromatics, and $C_9^+$ aromatics may be from a catalytic reforming unit where the feedstock naphtha is converted to an oil rich in aromatics which further undergoes the treatment of depentanizing and aromatics extraction etc. The benzene separated from this feed stream may be sent out the separation unit as a product. $C_{10}^+$ aromatics, if present in the feed stream, may also be separated from this feed stream and sent out the separation unit as a product, and the purity of $C_9$ aromatics in the separated $C_9^+$ aromatics stream may be further increased in this case.

In accordance with the present invention, the second $C_8$ aromatics has a high purity of the target product p-xylene, thus the second $C_8$ aromatics rich in p-xylene may or may not be further separated to extract the p-xylene product. It is preferable to send the second $C_8$ aromatics to a p-xylene separation unit. The separation of the p-xylene target product from the second aromatics stream may be conducted independently or with either or both of the first and the third aromatics stream together. Similarly, the separation of the p-xylene target product from the third aromatics stream may be conducted independently or with either or both of the first and second aromatics stream together. It is preferable that the separation of the p-xylene from the first, the second, and third $C_8$ aromatics stream is conducted in the same separation unit. The methods of separating the p-xylene product from the $C_8$ aromatics stream includes adsorptive separation and subzero crystallization separation etc.

After the target p-xylene is separated, the remaining mixed xylene is preferably sent to an isomerization unit to conduct the reaction of isomerization for converting the remaining mixed xylenes to the p-xylene. The effluent of the isomerization unit may be sent to a deheptanizer where a $C_8^+$A stream is withdrawn from the bottom, a stream containing benzene and toluene are withdrawn from the top. The $C_8^+$A stream may be sent to an aromatics fractionation unit first, and the $C_8$ aromatics separated may undergo a similar separation with the first, second, or the third $C_8$ aromatics stream as discussed above, so that the p-xylene product can be obtained.

The separation in the steps of a), c), and e) may be conducted independently or with either or both of the other two steps together. For example, the first effluent and the second effluent may enter the same aromatics fractionation unit as employed in the step of a). Similarly, the separation to $C_8^+$A stream derived from the isomerization unit may also be conducted independently or with at least one of the steps of a), c), and e) together.

In accordance with one preferred embodiment of the present invention the separation of the step of c) is specifically equipped with an aromatics fractionation unit so that it can be conducted independently. Preferably, the second $C_8$ aromatics stream is further separated into a part of the p-xylene product and a residual liquid by the subzero crystallization separation method. More preferably, the residual liquid may be admixed with the first and the third $C_8$ aromatics stream to form a mixture, and then the mixture may be separated into the p-xylene product and the remaining mixed xylene by the adsorptive separation method.

The normal operation conditions of the reaction zone of the toluene selective disproportionation unit may be a pressure of 1–4 MPa, a reaction temperature of 300–480° C., a hydrogen to hydrocarbon mole ratio of 0.5–10, and a liquid weight space velocity of 0.8–8 h$^{-1}$; the catalyst used in the toluene selective disproportionation unit may be a ZSM-type molecular sieve catalyst, and preferably a ZSM-5-type molecular sieve catalyst; the SiO$_2$/Al$_2$O$_3$ mole ratio of the ZSM-5-type molecular sieve is 15–100; the ZSM-5-type molecular sieve preferably contains 0.005–5%, preferably 0.01–1%, by weight of at least one metal or oxide of the element selected from the group consisting of platinum, molybdenum and magnesium. The normal operation conditions of the reaction zone of the disproportionation and transalkylation unit may be are a reaction pressure of 1–5 MPa, a reaction temperature of 250–480° C., a hydrogen to hydrocarbon mole ratio of 0.5–10, and a liquid weight space velocity of 0.8–8 h$^{-1}$, the content of C$_9$ aromatics in the feed is 5–60% by weight; the catalyst used in the disproportionation and transalkylation unit is at least one molecular sieve selected from the group consisting of β-zeolite, mordenite, and MCM-22, with β-zeolite or/and mordenite being preferred; the SiO$_2$/Al$_2$O$_3$ mole ratio of the molecular sieve is 10–100, preferably 10–50; the preferred catalyst is a catalyst containing metal bismuth or its oxide, the amount of which is 0.005–5% by weight, preferably 0.05–2% by weight. The toluene from the aromatics fractionation unit is preferably the toluene separated in the aromatics fractionation unit or the toluene separated in the aromatics fractionation unit and a foreign toluene from other available source as a supplement. The amount of the toluene entering into the toluene selective disproportionation unit is preferably 5–95%, more preferably 20–80% of the total amount of toluene. The weight ratio of the toluene feed to the C$_9^+$ aromatics in the disproportionation and transalkylation unit is 80/20–40/60.

In the toluene disproportionation and transalkylation unit of the present invention, the adopted bismuth-containing zeolite catalyst has the function to convert toluene and C$_9^+$A to xylenes and benzene in the presence of hydrogen through the disproportionation and transalkylation reactions. Because the decrease in the proportion of toluene and increase in the proportion of C$_9$A in the feedstock benefit the occurrence of the transalkylation reaction of toluene and C$_9$A$^+$, more C$_8$A is produced. In the toluene selective disproportionation unit, toluene selective disproportionation reaction takes place, as a result, toluene converts to p-xylene with high selectivity. This kind of process route not only can convert C$_9^+$A to xylenes, eliminating the harsh requirement to the feedstock, but also can convert toluene to mixed xylenes with a high content of p-xylene through the selective disproportionation, further raising the concentration of the p-xylene in the mixed xylene feed entering into the PX separation unit, facilitating the PX separation, and lowering the scale of the isomerization unit and the like, and thereby lowering the energy consumption of the whole aromatics complex and attaining a better technical effect. Besides, the present invention is especially applicable to the reconstruction of the existing aromatic complex for extension. The reconstruction is very simple: reserving the disproportionation and transalkylation, isomerization, p-xylene separation, and aromatics fractionation units as they are, setting up a new selective disproportionation unit. In this way, it is possible to increase the output of p-xylene and benzene by raising the capacity of the reforming unit or purchasing an adequate amount of toluene, and meanwhile, the energy consumption is obviously lowered and better effects are obtained.

Figure 2:
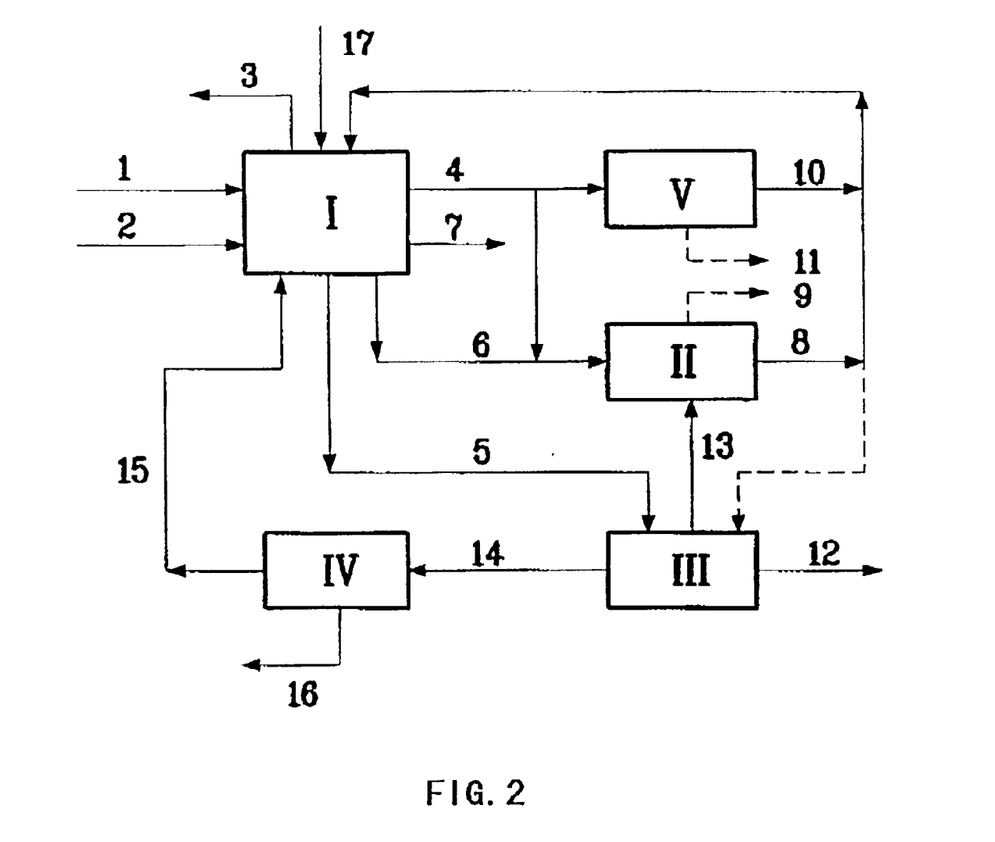
FIG. 2 is the flow diagram of the process for selective disproportionation and disproportionation and transalkylation of xylene+$C_9^+$A for producing p-xylene in accordance with one embodiment of the present invention.

Now referring to FIG. 1 and FIG. 2, I represents the aromatics fractionation unit, comprising a benzene separation tower, a toluene separation tower and a xylene separation tower, and optionally a heavy aromatics separation tower to be dependent on the concrete situation; II represents the disproportionation and transalkylation unit; III represents the PX separation unit; IV represents the isomerization unit; and V represents the toluene selective disproportionation unit. Whether units II and V are equipped with the independent aromatics separation device of their own depends on the concrete situation. Line 1 is the mixed stream of benzene and toluene, line 2 is the C$_8^+$A stream withdrawn from the bottom of the deheptanizer, line 3 is the high purity benzene product withdrawn from the top of the benzene tower, line 4 is the toluene withdrawn from the top of the toluene tower, line 5 is the C$_8$A withdrawn from the top of the xylene tower, line 6 is the C$_9$A and a part of C$_{10}$A withdrawn from the top of the heavy aromatics tower of the aromatics fractionation unit I, line 7 is C$_{10}^+$A withdrawn from the bottom of the heavy aromatics tower, line 8 is the effluent withdrawn from the bottom of the stabilization tower of the disproportionation and transalkylation unit, line 9 is the benzene product, line 10 is the effluent withdrawn from the bottom of the stabilization tower of the selective disproportionation unit, line 11 is the benzene product, line 12 is the high purity p-xylene product, line 13 is the small amount of toluene separated from the PX separation unit, line 14 is the mixed xylenes after separating PX, line 15 is the C$_8^+$A stream withdrawn from the bottom of the deheptanizer of the isomerization unit, and line 16 is the benzene- and toluene-containing stream withdrawn from the top of the deheptanizer of isomerization unit IV and line 17 is a foreign toluene.

The flow scheme of the traditional complex for producing aromatics is shown in FIG. 1. Benzene and toluene stream 1 from the aromatics extraction unit and the bottom effluent C$_8^+$A stream 2 of the deheptanizer of the catalytic reforming unit enter into the aromatics fractionation unit I separately and the separated benzene stream 3 and C$_{10}^+$A stream 7 are withdrawn as the products. Toluene stream 4 and C$_9^+$A stream 6 serve as the feed of toluene disproportionation and transalkylation unit II and mixed xylene stream 5 is fed to xylene separation unit III. Whether toluene disproportionation and transalkylation unit II is equipped with the aromatics separation device depends on the concrete situation. When the aromatics separation device is equipped, nitration grade benzene product 9 is withdrawn from the selective disproportionation unit and C$_8$A stream 8 enters into the PX separation unit to separate PX; when the toluene disproportionation unit is not equipped with the aromatics fractionationunit, bottom effluent 8 withdrawn from the stripping tower directly enters into the aromatics fractionation unit for separation. Target product p-xylene 12 is separated from p-xylene separation unit III, the small amount of toluene 13 returns to the toluene disproportionation unit, and other mixed xylenes 14 enter into xylene isomerization unit IV to conduct the isomerization reaction. C$_8^+$A stream 15 withdrawn from the bottom of deheptanizer of the isomerization unit is fed to the aromatics fractionation unit and benzene- and toluene-containing stream 16 withdrawn from the top of the deheptanizer is fed to the aromatics extraction unit.

The process flow scheme of the complex for producing aromatics in accordance with one embodiment of the present invention is shown in FIG. 2. Compared to the traditional process, the improvement of the present invention is the addition of a toluene selective disproportionation unit based on the traditional process and the corresponding modification of the process route. The similarity between FIG. 1 and FIG. 2 will not be described and the difference will be described bellow in detail. The present process divides the toluene 4 which entirely serves as the feed of the toluene disproportionation and transalkylation unit originally into two streams. One still serves as the feed of the toluene disproportionation transalkylation unit and the remaining toluene serves as the feed of toluene selective disproportionation unit V. Whether the selective disproportionation unit is equipped with the aromatics separation device depends on the concrete situation. When the aromatics separation device is equipped, nitration grade benzene product 11 is withdrawn from the selective disproportionation unit. The unreacted toluene is recycled, and p-xylene-rich $C_8A$ stream 10 enters into the subzero crystallization separation unit to separate PX; when the selective disproportionation unit is not equipped with the aromatics fractionation unit, bottom effluent 8 withdrawn from the stripping tower directly enters into the aromatics fractionation for separation, and no benzene stream 11 is withdrawn. Foreign toluene 17 enters the aromatics fractionation unit I as another stream of the feedstock.

The following examples illustrate the invention without limiting it.

EXAMPLE 1

The capacity for producing PX and energy consumption of the present invention was examined based on the composition of various substances of $C_6A$-$C_{10}^+$ aromatics in the aromatics stream withdrawn from the reforming unit of a typical aromatics complex as the fundamental data.

Table 1 is the composition of the aromatics withdrawn from a typical reforming unit and the flow rates of various components used in the present example.

TABLE 1 composition and flow rates of the reformed aromatics

| Component | Content, % | Flow rate, kg/h |
|---|---|---|
| Ben | 11.65 | 10000 |
| Tol | 43.09 | 37000 |
| $C_8A$ | 31.45 | 27000 |
| $C_9A$ | 11.51 | 9882 |
| $C_{10}^+A$ | 2.30 | 1976 |
| Σ | 100 | 85858 |

The feedstock shown in Table 1 and the aforesaid technique of the present invention (aromatics fractionation device is included in the selective disproportionation unit) are used to produce p-xylene. 75% of toluene stream 4 enters into the selective disproportionation unit, and the remaining 25% enters into the disproportionation and transalkylation unit. The weight ratio of toluene to $C_9A$ was 60/40. The catalyst used in the toluene selective disproportionation unit was a ZSM-5 molecular sieve with a $SiO_2/Al_2O_3$ mole ratio of 50, on which 0.1% by weight of platinum was supported; the reaction conditions were a reaction pressure of 1.5 MPa, a reaction temperature of 420° C., a hydrogen to hydrocarbon mole ratio of 3, and a liquid weight space velocity of 4 $h^{-1}$. The catalyst used in the toluene disproportionation unit was a mordenite molecular sieve with a $SiO_2/Al_2O_3$ mole ratio of 30, on which 0.8% by weight of bismuth was supported; the reaction conditions are a reaction pressure of 3.0 MPa, a reaction temperature of 360° C., a hydrogen to hydrocarbon mole ratio of 6, and a liquid weight space velocity of 1.5 $h^{-1}$. Under the above situations, the feed and effluent of the selective disproportionation unit, disproportionation and transalkylation unit, and isomerization unit are shown in Table 2, the treating scales of various units of the aromatics complex are shown in Table 3, the outputs of the products p-xylene and benzene are shown in Table 4.

TABLE 2

Process materials in Example 1

| | Component | Selective disproportionation unit | Disproportionation and transalkylation unit | Isomerization unit | Adsorptive separation unit | Xylene tower |
|---|---|---|---|---|---|---|
| Feed into unit, Kg/h | Ben | 11 | 3 | 0 | | 0 |
| | Tol | 86823 | 27698 | 125 | 125 | 125 |
| | $C_8A$ | 84 | 238 | 161555 | 21447 | 214661 |
| | $C_9A$ | / | 18908 | 41 | 41 | 18979 |
| | $C_{10}^+A$ | / | 657 | | | 3632 |
| | Σ | 86918 | 47505 | 161722 | 214613 | 237398 |
| Flow-out of unit, kg/h | Ben | 12006 | 3866 | 2061 | 0 | 0 |
| | Tol | 59799 | 16818 | 1043 | 125 | 125 |
| | $C_8A$ | 12195 | 15704 | 155915 | 214447 | 214661 |
| | $C_9A$ | 703 | 7540 | 825 | 41 | 18979 |
| | $C_{10}^+A$ | 20 | 1458 | | | 3632 |
| | Σ | 84723 | 45386 | 159844 | 214613 | 237398 |

Where Ben is benzene, Tol is toluene, $C_8A$ is $C_8$ aromatics, $C_9A$ is $C_9$ aromatics, and $C_{10}^+A$ is $C_{10}$ and higher aromatics.

TABLE 3

Treating scales of various units in Example 1

| Unit | Disproportionation and transalkylation unit | Isomerization unit | Adsorptive separation unit | Benzene/toluene fractionation unit | Xylene fractionation unit |
|---|---|---|---|---|---|
| Scale, kg/h | 47505 | 161722 | 210658 | 96240 | 233214 |

TABLE 4

Outputs and purities of the products in Example 1

| Product | Output, kg/h | Purity, % |
|---|---|---|
| p-xylene | 48936 | 99.8 |
| Benzene | 27933 | 99.94 |

The results show that the energy consumption was 575 Mkcal/t (p-xylene+benzene), which was reduced by 18% in the technique of the present invention relative to the 702 Mkcal/t (p-xylene+benzene) in the following Comparative Example 1. In the present invention, the weight concentration of the p-xylene in the mixed xylenes entering into the adsorptive separation unit was 23.0%, which was 20% higher than that in the Comparative Example 1 (19.2%).

EXAMPLE 2

By still using the process flow, process conditions, and catalyst in Example 1, the capacity of the technique of the present invention for producing PX was re-examined based on the composition of the feedstock and 22% more flow rate of the feed shown in Table 1. The composition and flow rate of the feed are shown in Table 5. The specific situations of the feed and effluent of the selective disproportionation unit, disproportionation and transalkylation unit, and isomerization unit are shown in Table 6, the treating scales of various units of the aromatics complex are shown in Table 7, and the outputs of the products p-xylene and benzene are shown in Table 8.

TABLE 5

Contents and flow rates of the reformed aromatics

| Component | Content, % | Flow rate, kg/h |
|---|---|---|
| Ben | 11.65 | 12200 |
| Tol | 43.09 | 45140 |
| $C_8A$ | 31.45 | 32940 |
| $C_9A$ | 11.51 | 12056 |
| $C_{10}^+HCs$ | 2.30 | 2410 |
| Σ | 100 | 104746 |

TABLE 6

Process materials in Example 2

| | Component | Selective disproportionation unit | Disproportionation and transalkylation unit | Isomerization unit | Adsorptive separation unit | Xylene tower |
|---|---|---|---|---|---|---|
| Feed into unit, Kg/h | Ben | 13 | 4 | 0 | 125 | 0 |
| | Tol | 105875 | 33847 | 153 | 125 | 125 |
| | $C_8A$ | 102 | 295 | 201195 | 214447 | 214661 |
| | $C_9A$ | / | 23106 | 50 | 41 | 18979 |
| | $C_{10}^+A$ | / | 3819 | | | 3632 |
| | Σ | 105991 | 61071 | 201397 | 214613 | 237398 |
| Flow-out of unit, kg/h | Ben | 14641 | 5323 | 2566 | 0 | 0 |
| | Tol | 72921 | 20535 | 1296 | 125 | 125 |
| | $C_8A$ | 14871 | 20126 | 194172 | 214447 | 214661 |
| | $C_9A$ | 857 | 9217 | 1026 | 41 | 18979 |
| | $C_{10}^+A$ | 24 | 2017 | | | 3632 |
| | Σ | 103314 | 57218 | 199060 | 214613 | 237398 |

TABLE 7

Treating scales of various units in Example 2

| Unit | Disproportionation and transalkylation unit | Isomerization unit | Adsorptive separation unit | Benzene/toluene fractionation unit | Xylene fractionation unit |
|---|---|---|---|---|---|
| Scale, kg/h | 61071 | 201397 | 261926 | 118380 | 289732 |

TABLE 8

Outputs and purities of the products in Example 2

| Product | Output, kg/h | Purity, % |
|---|---|---|
| p-xylene | 60528 | 99.8 |
| Benzene | 34731 | 99.94 |

Compared to Comparative Example 1, the treating capacity of the device in Example 2 increased by 22%, the output of p-xylene increased by 18.4%, and the output of benzene increased by 30.8%, while the treating scales of the other units did not increase except the selective disproportionation unit, which was not equipped in Comparative Example 1. The nearest treating capacities were in the adsorptive separation unit, but the treating capacity was only 99.8% of that in Comparative Example 1. Therefore, by using the technique of the present invention, the treating capacity of the device and the output of the products p-xylene and benzene can be increased.

EXAMPLE 3

By still using the process flow, process conditions, and catalyst in Example 1, the capacity of the technique of the present invention for producing PX was re-examined based on the flow rate of the feedstock shown in Table 1, but purchased 53000 kg/h pure toluene entered into the selective disproportionation unit. The specific situations of the feed and effluent of the selective disproportionation unit, disproportionation and transalkylation unit, and isomerization unit are shown in Table 9, the treating scales of various units of the aromatics complex are shown in Table 10, and the outputs of the products p-xylene and benzene are shown in Table 11.

TABLE 11

Outputs and purities of the products in Example 3

| Product | Output, kg/h | Purity, % |
|---|---|---|
| p-xylene | 73494 | 99.8 |
| Benzene | 51638 | 99.94 |

The results show that in the present example, the output of p-xylene increases by 45%, and the output of benzene increases by 197%, while the treating scales of the other units did not increase except the selective disproportionation unit, which was not equipped in Comparative Example 1. Therefore, by using the technique of the present invention, the treating capacity of the system and the outputs of the products p-xylene and benzene can be greatly increased by only setting up a new selective disproportionation unit containing an aromatics fractionation unit and purchasing an adequate amount of toluene, but keeping the scale of the original units unvaried. In addition, the weight concentration of the p-xylene in the mixed xylenes entering into the adsorptive separation unit increases by 29.6%.

EXAMPLE 4

By still using the process flow, process conditions, and catalyst in Example 1, and the same feedstock as Example 3, the capacity of the technique of the present invention for producing PX was re-examined, but the difference was that the process for separating the mixed xylenes produced by the toluene selective disproportionation changed from the adsorptive separation to the subzero crystallization separation. The treating scales of various units of the aromatics complex are shown in Table 12, and the outputs of the products p-xylene and benzene are shown in Table 13.

TABLE 9

Process materials in Example 3

| | Component | Selective disproportionation unit | Disproportionation and transalkylation unit | Isomerization unit | Adsorptive separation unit | Xylene tower |
|---|---|---|---|---|---|---|
| Feed into unit, Kg/h | Ben | 22 | 3 | 0 | | 0 |
| | Tol | 256328 | 31722 | 245 | 125 | 125 |
| | $C_8A$ | 201 | 288 | 183099 | 214447 | 214661 |
| | $C_9A$ | / | 21647 | 41 | 41 | 18979 |
| | $C_{10}^+A$ | / | 688 | | | 3632 |
| | Σ | 256551 | 54349 | 183386 | 214613 | 237398 |
| Flow-out of unit, kg/h | Ben | 34969 | 4392 | 2277 | 0 | 0 |
| | Tol | 177790 | 19261 | 1270 | 125 | 125 |
| | $C_8A$ | 35437 | 17858 | 176776 | 214447 | 214661 |
| | $C_9A$ | 2046 | 8839 | 922 | 41 | 18979 |
| | $C_{10}^+A$ | 57 | 1578 | | | 3632 |
| | Σ | 250299 | 51928 | 181245 | 214613 | 237398 |

TABLE 10

Treating scales of various units in Example 3

| Unit | Disproportionation and transalkylation unit | Isomerization unit | Adsorptive separation unit | Benzene/toluene fractionation unit | Xylene fractionation unit |
|---|---|---|---|---|---|
| Scale, kg/h | 54349 | 183386 | 256880 | 103347 | 82395 |

TABLE 12

Treating scales of various units in Example 4

| Unit | Disproportionation and transalkylation unit | Isomerization unit | Adsorptive separation unit | Benzene/toluene fractionation unit | Xylene fractionation unit | Subzero-crystallization unit |
|---|---|---|---|---|---|---|
| Scale, kg/h | 54323 | 182414 | 232553 | 103315 | 258054 | 37573 |

Thus, while there have shown and described and pointed out fundamental novel features of the invention as applied to a preferred embodiment thereof, it will be understood that various omissions and substitutions and changes in the form and details of the processes illustrated, and in their operation, may be made by those skilled in the art without departing from the spirit of the invention. For example, it is expressly intended that all combinations of those elements and/or method steps which perform substantially the same function in substantially the same way to achieve the same results are within the scope of the invention. Moreover, it should be recognized that elements and/or method steps shown and/or described in connection with any disclosed form or embodiment of the invention may be incorporated in any other disclosed or described or suggested form or embodiment as a general matter of design choice. It is the intention, therefore, to be limited only as indicated by the scope of the claims appended hereto.

We claim:

1. A process or the selective disproportionation of toluene and the disproportionation and transalkylation of toluene and $C_9^+$ aromatics comprising:
   a) separating a feed stream comprising benzene, toluene, $C_8$ aromatics, and $C_9^+$ aromatics into a first benzene stream, a toluene stream, a first $C_8$ aromatics stream, and a $C_9^+$ aromatics stream;
   b) introducing part of the toluene stream into a toluene selective disproportionation unit to conduct the toluene selective disproportionation reaction for producing a first effluent comprising $C_8$ aromatics rich in p-xylene, and benzene;
   c) separating a second $C_8$ aromatics stream and a second benzene stream from the first effluent produced in the step of b);
   d) introducing another part of the toluene stream and the $C_9^+$ aromatics stream into a toluene disportination and transalkylation unit to conduct the toluene disproportionation and transalkylation reaction in the presence of hydrogen for producing a second effluent comprising $C_8$ aromatics and bezene;
   e) separating a third $C_8$ aromatics stream and a third benzene stream from the second effluent produced in the step of d); and
   f) separating the first, and third $C_8$ aromatics stream into a p-xylene product and a remaining mixed xylenes stream.

2. The process of claim 1 further comprising a step of separating the second $C_8$ aromatics into the p-xylene product and the remaining mixed xylenes stream.

3. The process of claim 1 wherein the amount of the toluene introduced in the step of b) accounts for 5–95% of the total amount of the toluene introduced in the steps of b) and d).

4. The process of claim 1 wherein the amount of the toluene introduced in the step of b) accounts for 20–80% of the total amount of the toluene introduced in the steps of b) and d).

5. The process of claim 1 wherein the weight ratio of the toluene and the $C_9^+$ aromatics introduced in the step of d) is 80/20–40/60.

6. The process of claim 3 wherein the total amount of the toluene includes the toluene separated in the step of a) and a foreign toluene.

7. The process of claim 1 further comprising steps of sending the remaining mixed xylenes stream to an isomerization unit to conduct the reaction of isomerization for converting the remaining mixed xylenes to the p-xylene;
separating the p-xylene product from the effluent of the reaction of isomerization.

8. The process of claim 1 wherein a $C_{10}^+$ aromatics stream is also separated from the feed stream in the step of a) when the $C_{10}^+$ aromatics is present in the feed stream.

9. The process of claim 1 wherein the p-xylene is separated by utilizing an adsorptive separation method.

10. The process of claim 1 wherein the p-xylene is separated by utilizing a subzero crystallization separation method.

11. The process of claim 1 wherein the step of c) is conducted independently in an aromatics fractionation unit specifically equipped for the step of c), and the second $C_8$ aromatics stream is further separated into a part of the p-xylene product and a residual liquid by the subzero crystallization separation method.

12. The process of claim 11 further comprising steps of:
admixing the residual liquid with the first and the third $C_8$ aromatics stream to form a mixture; and
separating the mixture into the p-xylene product and the remaining mixed xylene by the adsorptive separation method.

13. The process of claim 1 wherein the reaction zone of the toluene selective disproportionation unit is normally operated at a reaction pressure of 1–4 MPa, a reaction temperature of 300–480° C., a hydrogen to hydrocarbon mole ratio of 0.5–10, and a liquid weight space velocity of 0.8–8 $h^{-1}$.

14. The process of claim 1 wherein the reaction zone of the disproportionation and transalkylation unit is normally operated at a reaction pressure of 1–5 MPa, a reaction temperature of 250–480° C., a hydrogen to hydrocarbon mole ratio of 0.5–10, a liquid weight space velocity of 0.8–8 $h^{-1}$, and a content of the $C_9^+$ aromatics of 5–60% by weight in the toluene stream an the $C_9^+$ aromatics stream introduced in the step of d).

15. The process of claim 1 wherein the toluene selective disproportionation unit is normally operated in the presence of a ZSM-type molecular sieve catalyst.

16. The process of claim 15 wherein the ZSM-type molecular sieve catalyst is a ZSM-5-type molecular sieve with a $SiO_2/Al_2O_3$ mole ratio of 15–100.

17. The process of claim 16 wherein the ZSM-type catalyst contains a 0.01–1% by weight of metal or oxide thereof, the metal is selected from the group consisting of platinum, molybdenum, magnesium, and combinations thereof.

18. The process of claim 1 wherein the disproportionation and transalkylation unit is normally operated in the presence of a molecular sieve type catalyst selected from the group consisting of β-zeolite, mordenite, MCM-22 and combinations thereof.

19. The process of claim 18 wherein the molecular sieve type catalyst is selected from the group consisting of β-zeolite, mordenite, and combinations thereof, the molecular sieve has a $SiO_2/Al_2O_3$ mole ratio of 15–50.

20. The process of claim 18 wherein the molecular sieve type catalyst contains 0.05–2% by weight of metal bismuth or its oxide.

* * * * *